(12) United States Patent
Krampert et al.

(10) Patent No.: US 10,517,761 B2
(45) Date of Patent: Dec. 31, 2019

(54) POSTOPERATIVE MODIFICATION OF AN INTRAOCULAR LENS

(71) Applicant: Carl Zeiss Meditec AG, Jena (DE)

(72) Inventors: Gerhard Krampert, Pleasanton, CA (US); Johannes Kindt, Weimar (DE); Daniel Bublitz, Rausdorf (DE); Robert Pomraenke, Jena (DE); Martin Kühner, Bad Klosterlausnitz (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 15/746,415

(22) PCT Filed: Jul. 6, 2016

(86) PCT No.: PCT/EP2016/066030
§ 371 (c)(1),
(2) Date: Jan. 21, 2018

(87) PCT Pub. No.: WO2017/012878
PCT Pub. Date: Jan. 26, 2017

(65) Prior Publication Data
US 2018/0200112 A1     Jul. 19, 2018

(30) Foreign Application Priority Data
Jul. 22, 2015   (DE) .................. 10 2015 009 610

(51) Int. Cl.
*A61F 9/008* (2006.01)
*A61B 3/10* (2006.01)
*A61B 3/14* (2006.01)

(52) U.S. Cl.
CPC .......... *A61F 9/00834* (2013.01); *A61B 3/102* (2013.01); *A61B 3/1005* (2013.01);
(Continued)

(58) Field of Classification Search
CPC ...... A61B 3/0025; A61B 3/103; A61B 3/1015; A61B 3/14; A61B 3/10
(Continued)

(56) References Cited

U.S. PATENT DOCUMENTS

2003/0189689 A1  10/2003 Rathjen
2006/0195076 A1  8/2006 Blumenkranz
(Continued)

FOREIGN PATENT DOCUMENTS

WO    WO 04/026198 A2    4/2004
WO    WO 2011/085274 A1  1/2011
WO    WO 2012/166696 A1  12/2012

OTHER PUBLICATIONS

PCT International Preliminary Report on Patentability and Written Opinion for International Application No. PCT/EP2016/066030, dated Feb. 1, 2018, 10 pages.
(Continued)

*Primary Examiner* — Mohammed A Hasan
(74) *Attorney, Agent, or Firm* — Patterson Thuente Pedersen, P.A.

(57) ABSTRACT

Systems and methods for localizing intraocular lens and/or existing refractive index patterns, to laser write-patterns, and to refractive index patterns in order to modify the refractive index by application of femtosecond laser pulses. OCT-based confocal detection and sectional image systems are provided for localization purposes, the systems being particularly suitable for the detection of phase patterns in addition to the localization of the IOL. With respect to laser write-patterns, the modification of existing refractive index patterns in the IOL is carried out by destroying existing structures or supplementing existing refractive index patterns.

17 Claims, 2 Drawing Sheets

(52) U.S. Cl.
CPC .............. *A61B 3/1025* (2013.01); *A61B 3/14* (2013.01); *A61F 9/0084* (2013.01); *A61F 9/00827* (2013.01); *A61F 2009/0087* (2013.01); *A61F 2009/00844* (2013.01); *A61F 2009/00851* (2013.01); *A61F 2009/00887* (2013.01)

(58) Field of Classification Search
USPC .......................................................... 351/205
See application file for complete search history.

(56) References Cited

U.S. PATENT DOCUMENTS

| | | |
|---|---|---|
| 2008/0001320 A1 | 1/2008 | Knox et al. |
| 2009/0005764 A1 | 1/2009 | Knox et al. |
| 2009/0036880 A1 | 2/2009 | Bischoff et al. |
| 2009/0143858 A1 | 6/2009 | Knox et al. |
| 2010/0228345 A1 | 9/2010 | Bille |
| 2011/0172649 A1* | 7/2011 | Schuele .................. A61F 9/008 606/4 |
| 2014/0135920 A1 | 5/2014 | Sahler et al. |
| 2014/0257257 A1* | 9/2014 | Grant .................. A61F 9/00802 606/4 |

OTHER PUBLICATIONS

PCT International Search Report and Written Opinion for International Application No. PCT/EP2016/066030, dated Sep. 27, 2016, 14 pages.

English translation of PCT International Search Report for International Application No. PCT/EP2016/066030, dated Sep. 27, 2016, 2 pages.

DE Search Report for 102015009610.9, dated Dec. 17, 2015, 11 pages.

\* cited by examiner

POSTOPERATIVE MODIFICATION OF AN INTRAOCULAR LENS

RELATED APPLICATIONS

This application is a National Phase entry of PCT Application No. PCT/EP2016/066030 filed Jul. 6, 2016 which application claims the benefit of priority to German Application No. 102015009610.9, filed Jul. 22, 2015, the entire disclosures of which are incorporated herein by reference.

BACKGROUND

For the treatment of cataracts, it has been the normal practice for decades to replace the natural lens with an artificial lens, a so-called intraocular lens, abbreviated IOL, in the framework of an invasive surgical operation.

Problems may arise after the insertion of the intraocular lens for various reasons, which impair the eyesight of the patient receiving the intraocular lens.

Thus, the refractive correction intended prior to the operation—by the selected inserted intraocular lens—may not actually be achieved after the operation. By way of example, the IOL calculation may have been inaccurate, or the IOL may have shifted during the healing process with regard to its position and/or orientation. This applies to both mono-focal as well as so-called multi-focal intraocular lenses.

Furthermore, it may be the case that after the operation, an implanted multi-focal lens may not be tolerated by a patient, e.g. due to sensitivity to glare.

It may also be the case that after the operation, the patient is not satisfied with the mono-focal intraocular lens, and would like to be able to see at a distance as well as close-up without needing glasses, thus desiring a multi-focal intraocular lens.

SUMMARY OF THE INVENTION

It would be advantageous in all of the above cases to be able to perform a retrospective modification of the inserted intraocular lens without a further invasive operation.

This can be achieved through the methods, techniques and structures disclosed in the patent applications US 2009/036880 Kempe, US 2008/001320, US 2009/143858, US 2009/005764, all of which are by Knox, and US 2010/228345, US 2014/135920, both of which are by Bille. These applications describe modification of the refractive index of an implanted intraocular lens through treatment of the lens with a femtosecond laser. These applications involve the precise parameters of the laser treatment, e.g. pulse energies, 0.05-1000 nJ, pulse durations 4-100 fs, or parameters for the refractive index patterns, e.g. typical modifications of the refractive index of the IOL through the laser of 0.001 to 0.03, axial expansions of the refractive index patterns of 5-50 µm, or the use, for example, of a so-called "wrapped-lens" refractive index pattern. Aside from the problems of the laser parameters and the type of index pattern, the problems of localizing the IOL in the eye and/or the refractive index pattern already present in the IOL, and determining the writing pattern for the laser in the IOL, in particular with repeated refractive index correction using a femtosecond laser, need to be solved for the practical application thereof.

Although solutions for locating the natural lens are already known, e.g. from WO04026198, Kempe, or US2006195076, Blumenkranz, locating an IOL that has no, or very little, diffusion in the volume of the IOL, and a focused, locally delimited specular reflection on the IOL surface, which is not always easy to detect, is more difficult.

It appears obvious to select the writing pattern of the laser, thus the pattern that the focal point of the laser follows when laser light or pulses are applied, such that it is the same as the refractive index pattern that is to be inscribed. This is the case with an initial correction. With repeated refractive index correction, however, it may be useful to allow for differences between the writing pattern and the refractive index pattern that is still to be inscribed.

DETAILED DESCRIPTION

Localization of the Intraocular Lens and the Refractive Index Pattern

Because a nominal position of the IOL in the eye is assumed for the calculation of the refractive index pattern that is to be inscribed, which is potentially measured prior to the calculation, this nominal position of the IOL must also be known during the writing. For this, the position and/or shape of the intraocular lens in the eye with respect to the laser system must first be determined, prior to writing the writing pattern in the implemented IOL. Furthermore, it must be checked whether there is enough space in the IOL for the intended refractive index pattern that is to be subsequently inscribed. This is relevant in particular when the type of implemented IOL is unknown because the invasive surgery for the implantation was a long time ago and no documentation is available.

Furthermore, for an IOL that has already been modified in a non-invasive manner through the above laser process, the dimensions and/or position of a previously inscribed refractive index pattern in an IOL must be known. This information is necessary for correcting a previously existing refractive index pattern with another refractive index pattern. Because the unmodified refractive index of the IOL deviates only slightly from the refractive index of the previously written refractive index, it is difficult to detect the refractive index pattern with classic imaging methods on the basis of reflection.

Figure 1:
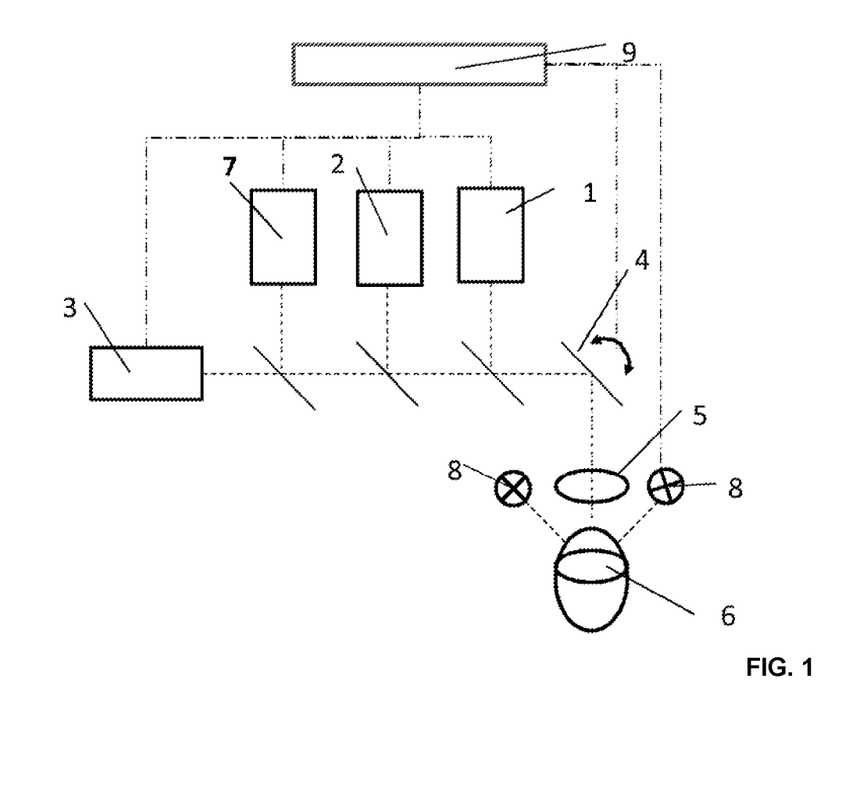
FIG. 1: A system for writing a refractive index pattern in an implanted IOL

A system A is disclosed for a refractive index modification of an IOL with a femtosecond laser, for identifying the position and/or shape of the IOL in the eye, and/or the dimensions and/or position of a pre-existing refractive index pattern, and modifying the refractive index of the IOL, comprising the following components (see FIG. 1):

A femtosecond pulse laser system that has a femtosecond laser source 1, a lens 5, which focuses the laser beam in the eye and the IOL 6, and a scanner 4, which scans the focal point of the laser beam laterally and axially to the optical axis of the lens. In one example variation, the lens itself is a scanning element.

An optical coherence tomography (OCT) measurement/imaging system that has an OCT light source/OCT detector 2 and a lateral scanner 4, which conducts the light of the OCT light source into the eye via the same lens that is used for the femtosecond pulse laser beam and detects the light reflected by the eye or its inner structures. In one example variation, the lateral scanner is the same as the lateral scanner for deflecting the femtosecond laser. In another example variation, the femtosecond pulse laser system is the same as the OCT light source.

A control device 9, which analyzes signals from the OCT system in order to determine the position and/or shape of the IOL in the eye, and which controls the femtosecond pulse laser system in order to apply the writing pattern in the IOL. In one example embodiment variation, the control device analyzes the signals from the OCT system in order to determine the position and/or expansion of a refractive index pattern inside the IOL in three dimensions.

System A enables a quick detection of the IOL and/or the refractive index pattern already present in the IOL, because a deep scanning can take place with modern spectral domain OCT methods such as SweptSource OCT more quickly than with the other systems presented below. Furthermore, a refractive index pattern can be detected very accurately with system A, because in addition to the modification of the refractive index, resulting in a reflection signal, the phase change over the course of the refractive index pattern can also be measured with an OCT. OCT readily detects such a phase change, while in contrast, the pure confocal detection is not affected by such phase changes.

As an alternative to the system A above, a system B is disclosed for a refractive index modification of an IOL with a femtosecond laser, for identifying the position and/or shape of the IOL in the eye, and/or the dimensions and/or position of a pre-existing refractive index pattern, and for modifying the refractive index of the IOL, comprising the following components, see FIG. 1:

A femtosecond pulse laser system that has a femtosecond laser source 1, a lens 5, which focuses the laser beam in the eye and the IOL 6, and a scanner 4, which scans the focal point of the laser beam laterally and axially to the optical axis of the lens. In one example variation, the lens itself is a scanning element.

A confocal detection measurement/imaging system that has a light source/detector 3 and a lateral scanner 4, which conducts the light of the light source into the eye via the same lens that is used for the femtosecond pulse laser beam, and detects the light reflected by the eye or its inner structures. In one example variation, the lateral scanner is the same as the lateral scanner for deflecting the femtosecond laser.

A control device 9, which analyzes signals from the confocal system, in order to determine the position and/or shape of the IOL in the eye, and which controls the laser system for the application of the writing pattern. In one example embodiment variation, the processor analyzes the signals from the confocal system in order to determine the position and/or expansion of a refractive index pattern inside the IOL in three dimensions.

In example variation B1, the confocal detector of system A is modified according to the principle of difference interference contrasts. For this, an optical element—e.g. a Wollaston prism—is inserted into the lighting and detection beam, which divides the lighting beam into two beams lying close to one another, and reunites the detection beams, such that an interference can be measured between the two beam paths in the detector. This enables the lateral detection of phase objects such as the refractive index pattern, when the object, in this case the IOL, is scanned laterally. The focal position along the optical axis is obtained through the detection confocality.

In an example variation B2, the confocal detector of system A is modified according to the principle of phase contrast. Complementary transmission filters and phase shifters are used in the lighting and detection beam paths for this. This also enables a lateral detection of phase objects such as the refractive index pattern when the IOL is scanned laterally. The focal position along the optical axis is obtained through the detection confocality.

System B has the advantage that the focus of the confocal detection system is in close alignment with the focal point of the femtosecond pulse laser system because the light of the confocal detection system passes through the same lens with the same or a similar aperture as the light of the femtosecond pulse laser system. This is the case in particular when the weakened and/or temporally extended femtosecond laser beam of the modification beam is used as the light source for the confocal detection system. Furthermore, because of its large detection aperture angle, the confocal detection is well suited for detecting specular reflections on curved surfaces, such as the boundary surfaces of an IOL that are not perpendicular to the lighting axis at all points. The system variations B1 and B2 improve the system B in that even phase objects, which are clearly indicated in the refractive index pattern, can be detected. However, a larger region must be scanned confocally to localize the refractive index pattern inside the IOL, which requires more time than detection through an A-scan in the system A OCT.

As an alternative to the above systems A and B, a system C is disclosed for a refractive index modification of an IOL with a femtosecond laser, for identifying the position and/or shape of the IOL in the eye, and/or the dimensions and/or position of the pre-existing refractive index pattern, and for modifying the refractive index of the IOL, comprising the following components:

A femtosecond pulse laser system that has a femtosecond laser source 1, a lens 5, which focuses the laser beam in the eye and the IOL 6, and a scanner 4, which scans the focal point of the laser beam laterally and axially to the optical axis of the lens. In one example variation, the lens itself is a scanning element.

A two dimensional measurement/imaging system, composed of a camera 7, which records at least two images of with the eye, and thus the IOL, lit from at least two different angles, and at least two light sources 8 for generating different lighting angles. When two images have been recorded that detect the light reflected by the object, the position and/or dimensions of the IOL in the eye can be determined. If two images are recorded with a phase contrast imaging process, the position of the refractive index pattern inside the IOL can be determined. The lateral position and the position along the optical axis can be determined through a triangulation of the two recordings made at known lighting angles with respect to the camera. The calculation is particularly simple when the pattern does not shift between the two recordings. The refractive index pattern then lies at the intersection of the two lighting axes and the observation axis, and in the focal region of the camera detection.

A control device 9, which analyzes signals from the confocal system in order to determine the position and/or shape of the IOL in the eye and controls the laser system for the application of the writing pattern. In one example embodiment variation, the control device analyzes the signals from the OCT system in order to record the position and/or expansion of a refractive index pattern in the IOL in three dimensions.

System C has the advantage over system B and the scanning embodiments of system A, in that a time consuming scanning of the object is not necessary for the localization. Nevertheless, the lateral and axial correlation of image coordinates in the camera system and the focal positioning positions of the femtosecond laser system are more complicated, and require calibration on a phantom eye.

In order to compensate for the disadvantages of the respective systems, combined systems are also conceivable.

As an alternative to the above systems A, B and C, a system D is disclosed for a refractive index modification of an IOL with a femtosecond laser, for identifying the position and/or shape of the IOL in the eye, and/or the dimensions and/or position of the pre-existing refractive index pattern and for modifying the refractive index of the IOL, comprising the following components:

A femtosecond pulse laser system that has a femtosecond laser source 1, a lens 5, which focuses the laser beam in the eye and the IOL 6, and a scanner 4, which scans the focal point of the laser beam laterally and axially to the optical axis of the lens. In one example variation, the lens itself is a scanning element.

An optical coherence tomography (OCT) measurement/imaging system that has an OCT light source/detector 2 and a lateral scanner 4, which conducts the light of the OCT light source into the eye through the same lens 5 as the femtosecond pulse laser beam, and detects the light reflected by the eye or its inner structures. In one example variation, the lateral scanner is the same as the lateral scanner for deflecting the femtosecond laser. In another example variation, the femtosecond pulse laser system is the same as the OCT light source.

A confocal detection measurement/imaging system that has a light source/detector 3 and a lateral scanner 4, which conducts the light of the light source into the eye via the same lens that is used for the femtosecond pulse laser beam, and detects the light reflected by the eye or its inner structures. In one example variation, the lateral scanner is the same as the lateral scanner for deflecting the femtosecond laser.

A control device 9, which analyzes signals from the confocal system in order to determine the position and/or shape of the IOL in the eye, which analyzes the signals of the OCT system in order to record the position and/or expansion of a refractive index pattern inside the IOL in three dimensions, and which controls the laser system for the application of the writing pattern.

With such a system D, the speed and reliability in locating a refractive index pattern inside the IOL through OCT is combined with the precision and reliability of the localization of the IOL surfaces through a confocal detector and the high degree of correlation between the focal positions of the confocal detection system and the femtosecond pulse laser system.

Writing Pattern of the Femtosecond Pulse Laser, Refractive Index Pattern

Following the detection of the intraocular lens and/or a pre-existing refractive index pattern, it must be determined which of the refractive index patterns are to be present after the treatment, and where a refractive index pattern is to be inscribed inside the IOL, or where it is to be inscribed in relation to pre-existing refractive index patterns.

With this writing of a refractive index pattern by a femtosecond pulse laser, a distinction should be made between the writing pattern of the laser, the pattern that the activated laser light or the applied laser pulse follows or maps during the scanning in the IOL in a coherent treatment sequence, and the refractive index pattern that is generated thereby. IOL materials exist, specifically, the refraction indexes of which can be modified through a laser treatment, in that the molecular structure is modified locally through interaction with the laser pulses and as a result, e.g., retains more water than previously. However, the molecular structure changes very little when a previously treated location is subjected to a further laser treatment. It also does not retain substantially more new water, such that the refractive index is also not modified. Thus, if a writing pattern precisely traces a previously generated refractive index pattern spatially, a new inscribed refractive index pattern is not created. If a writing pattern and a previously generated, existing refractive index pattern overlap, then only the portion of the writing pattern lying on a region of the IOL that was not previously inscribed is added to the previously generated refractive index pattern as a new, so-called supplementary, refractive index pattern.

Moreover, there are laser parameter/IOL material combinations that delete a previously inscribed, existing refractive index pattern. This requires a different laser parameter set than that used for writing the refractive index pattern. The deletion can also result in saturation effects, which are analogous to those specified above for the writing of patterns.

For many laser parameter/IOL material combinations, however, the writing of a refractive index pattern is irreversible, and cannot be sufficiently saturated.

Methods and method variations for refractive index modification in an intraocular lens with a femtosecond pulse shall be presented below. These can be executed with the systems A, B, C and D described in the preceding section.

Figure 3:
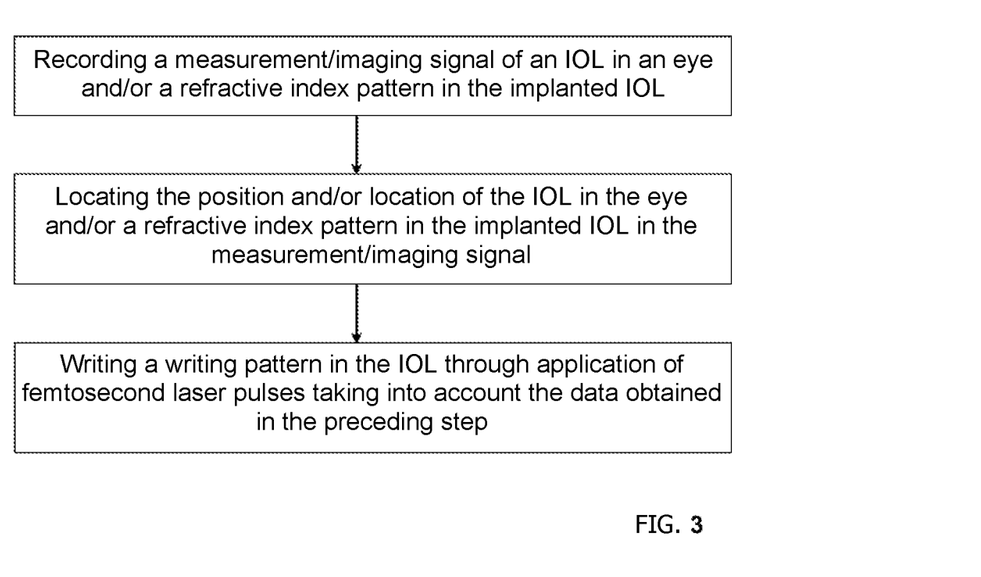
FIG. 3: A flow chart for obtaining a writing pattern for a femtosecond laser in an implanted IOL

A method is disclosed for refractive index modification of an IOL by means of femtosecond laser pulses, composed of the following steps—see FIG. 3:

1. Recording a measurement/imaging signal of the eye, or structures in the eye, in particular an IOL, e.g. in the form of a so-called A-scan or B-scan, or in three dimensions with an OCT system or corresponding confocal or 2D imaging signals.
2. Locating the position and/or location of the IOL in the eye in the measurement/imaging signal, e.g. by a control device.
3. Writing a writing pattern of femtosecond laser pulses in the IOL, e.g. with the femtosecond laser system, taking into account the data regarding the position and/or location of the IOL in the eye obtained in step 2, such that the, potentially supplementary, refractive index pattern obtained through the writing pattern is inscribed at an intended, nominal location inside the IOL.

By writing a writing pattern of femtosecond laser pulses in the IOL, the already implanted IOL can be converted into an IOL that has a modified refractive power, if the axial position of the IOL in the eye deviates from the intended location of the IOL in the implantation. By way of example, the focus of a mono-focal lens, or one or more foci of a multi-focal lens can be modified axially along the optical axis of the lens.

By writing a writing pattern of femtosecond laser pulses in the IOL, the already implanted IOL can be converted into an IOL that has additional optical prismatic effects, if the location of the IOL in the eye deviates from the planned location during the implantation, e.g. the IOL has tilted in relation to an optical axis of the eye, or the IOL is no longer centered in relation to an optical axis of the eye, or the IOL has rotated in relation to its optical axis, by writing, e.g., a wedge-shaped or diffractive, or appropriately wrapped writing pattern, potentially a supplementary refractive index pattern.

By writing a writing pattern of femtosecond laser pulses in the IOL, it can be converted to a mono-focal IOL, if a previously implanted multi-focal lens is not tolerated by a patient.

By writing a writing pattern of femtosecond laser pulses in the IOL, this mono-focal IOL can be converted to a multi-focal IOL if a patient with a previously implanted mono-focal IOL would like to be able to see distances and at close-range. By writing a writing pattern of femtosecond laser pulses in the IOL, the focal position of the implanted lens can be modified, if a patient with a previously implanted IOL experiences a retinal disease, or an existing retinal disease becomes more severe, e.g. a dry macular degeneration, after the implantation. The change in the focal position of the IOL can be a lateral displacement in relation to the optical axis of the eye, obtained by writing a wedge-shaped or diffractive refractive index pattern in the IOL.

In an example variation on step 1, a confocal signal and an OCT signal of the eye or structures of the eye can be recorded by a confocal detection system and an OCT system, respectively. In an example variation on step 2 with a supplementary step 2.1, the position and/or location and/or dimensions of an existing refractive index pattern inside the IOL can be located by a control device. Alternatively, or in addition to step 2.1, the positions and/or locations of markers can be located with reflection contrast in a step 2.2, wherein the markers are in predefined lateral and axial positions in relation to a previously inscribed refractive index pattern, e.g. in relation to the geometric axis of the IOL.

In one example variation, step 3 can be supplemented with the following steps:

3.1 Writing a writing pattern of femtosecond laser pulses into the IOL, wherein the data regarding the position and/or location and/or dimensions of a refractive index pattern inside the IOL obtained in step 2.1 or 2.2 are taken into account. It is thus possible to place the writing pattern at the intended, nominal position in relation to existing refractive index patterns.

3.2 As an alternative, or in addition to any of the preceding steps 3 (see FIG. 2): writing a first writing pattern 10 of femtosecond laser pulses in a previously untreated IOL 9, axially—with respect to the optical axis of the IOL—at least 200 µm posterior to the anterior IOL surface, for example posterior to the equator axis 11 or posterior to the middle of the IOL.

3.3 As an alternative, or in addition to any of the preceding steps 3: writing another writing pattern to correct a previously existing refraction index pattern or inscription pattern. This enables multiple corrections, e.g. even when the first correction is insufficient from the patient's perspective. Alternatively, a diffractive or wrapped writing pattern can be written after writing a supplementary refractive index pattern. For example, further writing patterns are inscribed axially in relation to the eye axis, anterior to the previously existing refractive index patterns. This ensures that the previously existing refractive index patterns do not need to be taken into account for the lateral and axial focal control of the treatment laser.

3.4 As an alternative, or in addition to any of the preceding steps 3: writing a first or second writing pattern of femtosecond laser pulses into the IOL in order to correct a previously existing multi-focal structure of the IOL, at most 200 µm posterior or anterior to the previously existing multi-focal structure. As a result, the previously existing multi-focal structure is corrected in terms of its optical effects by the newly inscribed refractive index pattern, before a significant and difficult to correct overlapping of the light beams of different orders from different regions of the multi-focal structure results.

3.5 As an alternative, or in addition to any of the preceding steps 3 (see FIG. 2): writing a writing pattern of femtosecond laser pulses—encompassed by an edge 11—surrounding or embedding previously existing refractive index patterns 10. This results in a supplementary refractive index pattern 12 surrounding the previously existing refractive index pattern. It is advantageous when a previously existing diffractive or wrapped refractive index pattern 10 on a simple geometric refractive index pattern, e.g. in the form of a cube or lens—which has an edge 11—is supplemented or filled in by the supplementary refractive index pattern 12. These simple geometric patterns, the optical effects of which, from existing and supplementary refractive index patterns, are not diffractive and do not correspond to a "wrapped lens," can be more easily taken into account when writing a further writing pattern, both by the calculation of the laser focus positions—which can be disrupted by diffractive or wrapped structures—as well as in the selection of a further refractive index pattern for obtaining the desired overall refraction of the IOL. Such filling in on simple geometric patterns is particularly advantageous for the writing of a further, diffractive or wrapped refractive index pattern 13 due to the higher tolerances regarding the axial and lateral positions—in relation to the optical axis of the eye—of the diffractive or wrapped pattern in relation to the simple geometric pattern with respect to the smaller tolerances in the positions between two diffractive patterns, when there is no filling in. For a saturating laser parameter/material combination, it is particularly advantageous when the writing pattern and the previously existing refractive index pattern overlap. In this case, the writing pattern, identified by the edge 11, also entirely or partially covers the region of the previously existing refractive index pattern 10. With these combinations, the refractive index is not altered by the second treatment in the overlapping regions. This is advantageous because a coherent and uninterrupted refractive index pattern that has an edge 11 is obtained in a more reliable manner, and because in this case, a laterally and axially precise, and thus time consuming, positioning of a further writing pattern 13 with respect to the refractive index pattern 11 existing prior to the further writing pattern is unnecessary. The further writing pattern 13 can be written thereby, with or without a spacing to the previously existing refractive index pattern 11.

Figure 2:
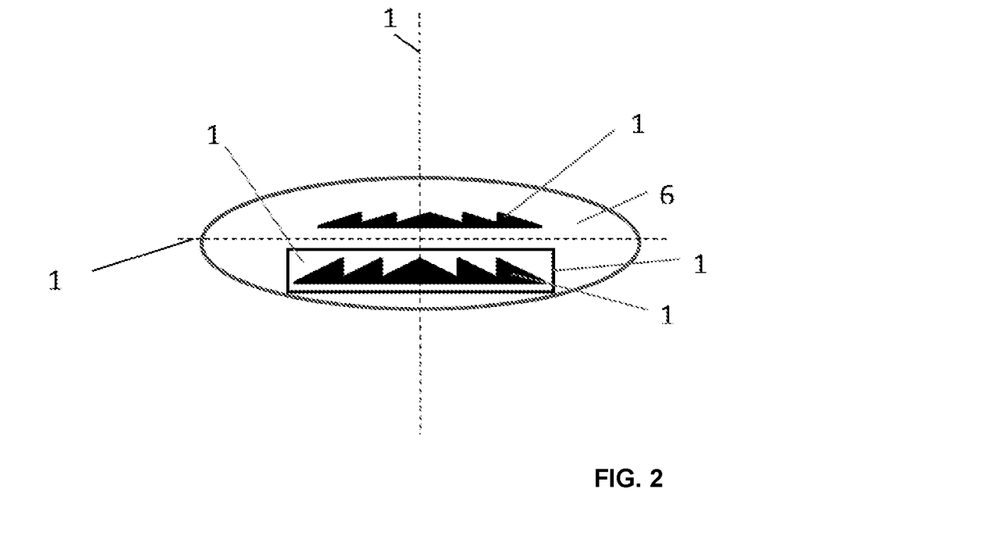
FIG. 2: A writing pattern for a femtosecond laser in an implanted IOL

3.6 As an alternative, or in addition to any of the preceding steps 3: writing a writing pattern of femtosecond laser pulses on a pre-existing refractive index pattern, wherein the laser parameters are selected such that the existing refractive index is reset to the original refractive index—a so-called erasing writing pattern. As a result, e.g., pre-existing diffractive or wrapped refractive index patterns are reset, such that they no longer need to be taken into account when writing a further refractive index pattern. For a saturating laser parameter/material combination, it is particularly advantageous when the writing pattern completely covers the pre-existing refractive index pattern, as well as overlapping portions of the IOL region that have not yet been inscribed, thus basically extending over the edge the pre-existing refractive index pattern. This is advantageous because it is a reliable means for obtaining an IOL that has the original, homogenous refractive index, and a precise lateral and axial, and thus time-consuming, positioning of another writing pattern 13 with respect to the pre-existing refractive index pattern 11 is no longer necessary.

3.7 As an alternative, or in addition to any of the preceding steps 3: writing a reflection marker in the IOL, e.g. with the use of femtosecond laser parameters, resulting in irreversible incisions in the IOL, and exhibiting a fixed lateral and axial relationship—with respect to the geometric axis of the IOL—to the writing patterns inscribed in step 3.

It is furthermore possible to execute the following example method for refractive index modification of an intraocular lens with a femtosecond laser pulse using the example system D.

A method B is disclosed for refractive index modification of an IOL by means of femtosecond laser pulses, composed of the following steps:

1. Recording a confocal signal and an OCT signal of the eye or structures in the eye, e.g. by the confocal detection system and the OCT system respectively.
2. Locating the position and/or location of the IOL in the eye with respect to the coordinate system of the confocal detection system in the confocal signal. Locating the position and/or location of the IOL in the eye with respect to the coordinate system of the OCT system in the OCT signal. Calculation of a coordinate transformation of the IOL position/location data obtained for the coordinate system of the OCT system to the IOL position/location data obtained for the coordinate system of the confocal system. Locating the position and/or location and/or dimensions of a refractive index pattern inside the IOL with respect to the coordinate system of the OCT system in the OCT signal. Conversion of the location of the refractive index pattern in the coordinate system of the OCT system on the basis of the coordinate transformation to a location with respect to the coordinate system of the confocal detection system. These calculations can be executed, e.g. by a control device.
3. Writing a writing pattern of femtosecond laser pulses in the IOL, e.g. with the femtosecond laser system, taking into account the data obtained in step 2 from the confocal signal regarding the position and/or location of the IOL in the eye, and taking into account the data obtained in step 3 regarding the position/location/dimensions of the refractive index pattern with respect to the coordinate system of the confocal detection system. Transformation to coordinates with respect to the confocal detection system on the basis of the concrete eye better ensures that the writing pattern is written at the intended, nominal location inside the IOL than calibration on a phantom eye.

The variations that have already been listed as variations on method A are also possible with this method B, as variations thereon. In particular, the variations 3.2-3.7 can be used as variations for method B.

LIST OF REFERENCE SYMBOLS 1 femtosecond light source
2 OCT light source and OCT detector
3 light source and detector for a confocal system
4 scanner mirror
5 focusing optics
6 IOL in the eye
7 2D camera
8 splitter projector
9 control device
10 previously written refractive index pattern
11 outer edge of the writing pattern
12 supplemented refractive index pattern
13 new writing pattern
14 axis of symmetry for the IOL along the optical axis of the eye
15 equatorial axis of the IOL

The invention claimed is:

1. A system for refractive index modification of an IOL with a femtosecond laser, comprising:
   a femtosecond pulse laser system that has a femtosecond laser source, a lens, which focuses the laser beam in the eye and the IOL, and a scanner, which scans the focal point of the laser beam laterally and axially to the optical axis of the lens;
   an optical coherence tomography (OCT) measurement/imaging system that has an OCT light source/OCT detector and a lateral scanner, which conducts the light of the OCT light source into the eye via the same lens that is used for the femtosecond pulse laser beam and detects the light reflected by the eye or its inner structures and in which the OCT measurement/imaging system is adapted to locate at least one of a position, a location or dimensions of a pre-existing refractive index pattern inside the IOL;
   a control device, which analyzes signals from the OCT system to determine a position of the IOL in the eye, a shape of the IOL or both a position and a shape of the IOL in the eye, and which controls the femtosecond pulse laser system to apply a writing pattern in the IOL.

2. A system for refractive index modification of an IOL with a femtosecond laser, comprising:
   a femtosecond pulse laser system that has a femtosecond laser source, a lens, which focuses the laser beam in the eye and the IOL, and a scanner, which scans the focal point of the laser beam laterally and axially to the optical axis of the lens;
   an optical coherence tomography (OCT) measurement/imaging system that has an OCT light source/detector and a lateral scanner, which conducts the light of the OCT light source into the eye also through the lens which focuses the laser beam in the eye, and detects the light reflected by the eye or its inner structures and in which the OCT measurement/imaging system is adapted to locate at least one of a position, a location or dimensions of a pre-existing refractive index pattern inside the IOL;
   a confocal detection measurement/imaging system that has a light source/detector and a lateral scanner, which conducts the light of the light source into the eye also through the lens which focuses the laser beam in the eye, and detects the light reflected by the eye or its inner structures;

a control device, which analyzes signals from the confocal system in order to determine the position and/or shape of the IOL in the eye, which analyzes the signals of the OCT system in order to record the position and/or expansion of a refractive index pattern inside the IOL in three dimensions, and which controls the laser system for the application of the writing pattern.

3. The system according to claim 2, wherein the lens acts as a scanning element.

4. The system according to claim 2, wherein the scanner and the lateral scanner are the same scanner.

5. A method for refractive index modification of an IOL by application of femtosecond laser pulses, comprising:
  recording a measurement and imaging signal of the eye or of structures in the eye;
  locating a position of the IOL, a location of the IOL in the eye or both a position and a location of the IOL in the eye in the measurement and imaging signal;
  locating at least one of a position, a location or dimensions of a pre-existing refractive index pattern inside the IOL; and
  writing a writing pattern of femtosecond laser pulses in the IOL, taking into account data obtained regarding the position, the location or both the position and the location of the IOL in the eye.

6. The method according to claim 5, further comprising: writing a first writing pattern in a previously untreated IOL, axially posterior—with respect to an optical axis of the IOL—to a middle of the previously untreated IOL.

7. The method according to claim 5, further comprising: writing a first or further writing pattern of femtosecond laser pulses in the IOL to correct a previously existing multi-focal structure of the IOL, at most 200 µm posterior or anterior to the previously existing multi-focal structure.

8. The method according to claim 5, further comprising writing the writing pattern in the IOL to convert:
  a mono-focal IOL into a multi-focal IOL,
  a multi-focal IOL into a mono-focal IOL, or
  a non-prismatic IOL into an IOL with a supplementary prismatic effect.

9. A method for refractive index modification of an IOL by application of femtosecond laser pulses, comprising:
  recording a measurement and imaging signal of the eye or of structures in the eye;
  locating a position of the IOL, a location of the IOL in the eye or both a position and a location of the IOL in the eye in the measurement and imaging signal; and
  writing a writing pattern of femtosecond laser pulses in the IOL, taking into account data obtained regarding the position, the location or both the position and the location of the IOL in the eye;
  locating at least one of a position, a location or dimensions of a pre-existing refractive index pattern inside the IOL;
  writing the writing pattern of femtosecond laser pulses in the IOL, taking into account, in addition to the data obtained regarding the position, the location or both the position and the location of the IOL in the eye, data regarding at least one of the position, location or dimensions of a refractive index pattern inside the IOL.

10. The method according to claim 9, further comprising: writing a further writing pattern to correct a previously existing refractive index pattern or writing pattern.

11. The method according to claim 10, comprising writing the further writing pattern at an axial position to the eye axis, anterior to the previously existing refractive index pattern.

12. The method according to claim 10, further comprising writing a writing pattern such that it surrounds or embeds a pre-existing refractive index pattern.

13. The method according to claim 12, wherein the pre-existing refractive index pattern and the supplemented refractive index pattern collectively form a geometrically simple, coherent refractive index pattern that does not have a diffractive optical effect, or an optical effect corresponding to a wrapped lens.

14. The method according to claim 12, wherein the writing pattern and the previously existing refractive index pattern overlap.

15. The method according to claim 10, wherein the previously existing refractive index pattern is erased by the writing pattern.

16. The method according to claim 10, wherein the writing pattern completely covers the previously existing refractive index pattern, and also covers parts of the IOL region that has not been inscribed.

17. The method according to claim 9,
  further comprising using OCT signals to calculate the position of the refractive index pattern and the position of the IOL in relation to the coordinate system of an OCT system,
  further comprising using confocal detection signals to calculate the position of the IOL in relation to the coordinate system of a confocal detection system,
  further comprising calculating a coordinate transformation of the IOL position in relation to the coordinate system of the OCT system and the IOL position in relation to the coordinate system of the confocal detection system,
  further comprising converting the position of the refractive index pattern in relation to the coordinate system of the OCT system on the basis of the coordinate transformation to a position of the refractive index pattern in relation to the coordinate system of the confocal detection system, and
  further comprising using position data of the IOL and the refractive index pattern in relation to the coordinate system of the confocal detection system for calculating the writing pattern.

* * * * *

UNITED STATES PATENT AND TRADEMARK OFFICE
CERTIFICATE OF CORRECTION

PATENT NO. : 10,517,761 B2
APPLICATION NO. : 15/746415
DATED : December 31, 2019
INVENTOR(S) : Gerhard Krampert et al.

It is certified that error appears in the above-identified patent and that said Letters Patent is hereby corrected as shown below:

In the Specification

Column 2, Line 15, delete "IOL" and insert --IOL.--

Column 2, Line 17, delete "IOL" and insert --IOL.--

Column 2, Line 19, delete "IOL" and insert --IOL.--

Signed and Sealed this
Seventh Day of April, 2020

Andrei Iancu
*Director of the United States Patent and Trademark Office*